United States Patent [19]

Nozoe et al.

[11] Patent Number: 5,204,459
[45] Date of Patent: Apr. 20, 1993

[54] PROCESS FOR PREPARING CARBAPENEM COMPOUNDS

[75] Inventors: Shigeo Nozoe; Tomihisa Ohta, both of Sendai, Japan

[73] Assignee: Ajinomoto Co., Inc., Tokyo, Japan

[21] Appl. No.: 853,069

[22] Filed: Mar. 17, 1992

Related U.S. Application Data

[62] Division of Ser. No. 661,246, Feb. 27, 1991, Pat. No. 5,118,831, which is a division of Ser. No. 360,534, Jun. 2, 1989, Pat. No. 5,028,718, which is a division of Ser. No. 95,445, Sep. 11, 1987, Pat. No. 4,876,383.

[30] Foreign Application Priority Data

Sep. 12, 1986 [JP] Japan .................. 61-215093

[51] Int. Cl.$^5$ ........................... C07D 487/04
[52] U.S. Cl. ................... 540/302; 540/350; 540/310
[58] Field of Search ............ 540/302, 350; 514/192, 514/195

[56] References Cited

U.S. PATENT DOCUMENTS 4,344,885  8/1982  Liu et al. ............... 540/302
4,499,278  2/1985  Mellillo et al. ......... 540/302

Primary Examiner—Nicholas S. Rizzo
Attorney, Agent, or Firm—Oblon, Spivak, McClelland, Maier & Neustadt

[57] ABSTRACT

Novel amino acid derivatives of the formula

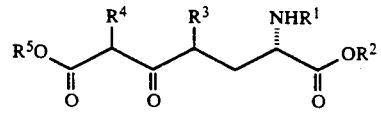

wherein $R^1$ is a protecting group removable under reducing or acid conditions, and $R^2$ and $R^5$ are hydrogen or carboxylic protecting groups, are useful as intermediates in preparing stereospecific carbapenam/carbapenem derivatives. $R^1$ is removed under reducing conditions to form a pyrrolidine derivative, which is further cyclized from the $R^5=H$ compound to form a β-lactam ring. Stereospecificity at the 6-position is achieved by treatment with lithium diisopropylamide (LDA) and quenching at different temperatures. Compound (I) can be prepared by treating $R^1$-protected $R^3$-pyrrolidone carboxylic acid $R^2$-ester with a lithium enolate of the formula $R^4CHLiCO_2R^5$. The lithium enolate can be formed from $R^4CH_2CO_2R^5$ by treatment with LDA.

5 Claims, No Drawings

PROCESS FOR PREPARING CARBAPENEM COMPOUNDS

This is a division of application Ser. No. 07/661,246, filed Feb. 27, 1991, now U.S. Pat. No. 5,118,831, which is a division of Ser. No. 360,534, filed Jun. 2, 1989, now U.S. Pat. No. 5,028,718, which is a division of Ser. No. 07/095,445, filed Sep. 11, 1987, now U.S. Pat. No. 4,876,383.

BACKGROUND OF THE INVENTION

1. Field of the Invention

The present invention concerns novel amino acid derivatives, and their production and uses as intermediates for production of a carbapenam or carbapenem, which is being developed as a drug, for example, an antibiotic having a β-lactam structure.

2. Discussion of the Background

It is known that carbapenem can be produced by bacteria (Kahan et al, J. Antibiotics 32, 1 (1979)), but it is an unstable compound, and in bacterial production the yield is low.

Synthetic methods for its production have been proposed, using as starting materials for example L-aspartic acid (T.N. Saltsmann et al, J. Amer. Chem. Soc., 102, 6161 (1980)); penicillin (S. Karady et al, J. Amer. Chem. Soc., 103, 6765 (1981)); L-threonine (M. Shiozaki et al, Tetrahedron Letters, 5202 (1981)); or D-glucose (N. Ikota et al, Chem. Pharm. Bul., 30, 1929 (1982)). However, prior synthetic processes have problems in that they are complex, the yield is low, and it is difficult to obtain a compound possessing several substituent groups because of the cyclization reaction required to form the five membered ring after the β-lactam ring has been formed.

SUMMARY OF THE INVENTION

The present invention provides novel amino acid derivatives represented by the general formula (I) having the (S) configuration in the α-position of the amino group,

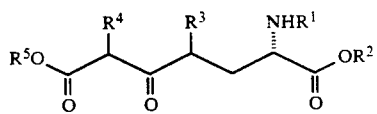

(I)

wherein $R^1$ is an organic group capable of being removed under reducing or acidic conditions, for example benzyloxycarbonyl, p-nitrobenzyloxycarbonyl, p-methoxybenzyloxycarbonyl and t-butyloxycarbonyl; $R^2$ and $R^5$ are, independently, hydrogen or a carboxylic-protecting group, for example, alkyl such as methyl, ethyl, i-propyl, and t-butyl, aralkyl such as benzyl and p-nitrobenzyl or alkaryl such as t-butylphenyl; $R^3$ is hydrogen, alkyl such as methyl, ethyl and propyl, hydroxy, methoxy or acetoxy; $R^4$ is methyl, ethyl, i-propyl, propyl, benzyl or an organic group represented by $CH_3CR^6(OR^7)$—in which $R^6$ is hydrogen or methyl, and $R^7$ is hydrogen or a hydroxyl-protecting group, for example, benzyl, benzyloxycarbonyl, t-butyldimethylsilyl or trichloroethyloxycarbonyl. Such derivatives are very useful as intermediates for production of a carbapenam or carbapenem and moreover can be produced in high yield. The invention therefore also includes methods for the production of carbapenem and carbapenam compounds using these intermediates, and methods for the production of the intermediates.

DETAILED DESCRIPTION OF THE PREFERRED EMBODIMENTS

A route for synthesizing the amino acid derivative (I) from a pyrrolidone carboxylic acid derivative and for synthesizing a carbapenam or carbapenem, therefrom is illustrated as follows ($R^{1-7}$ have the same meaning as above):

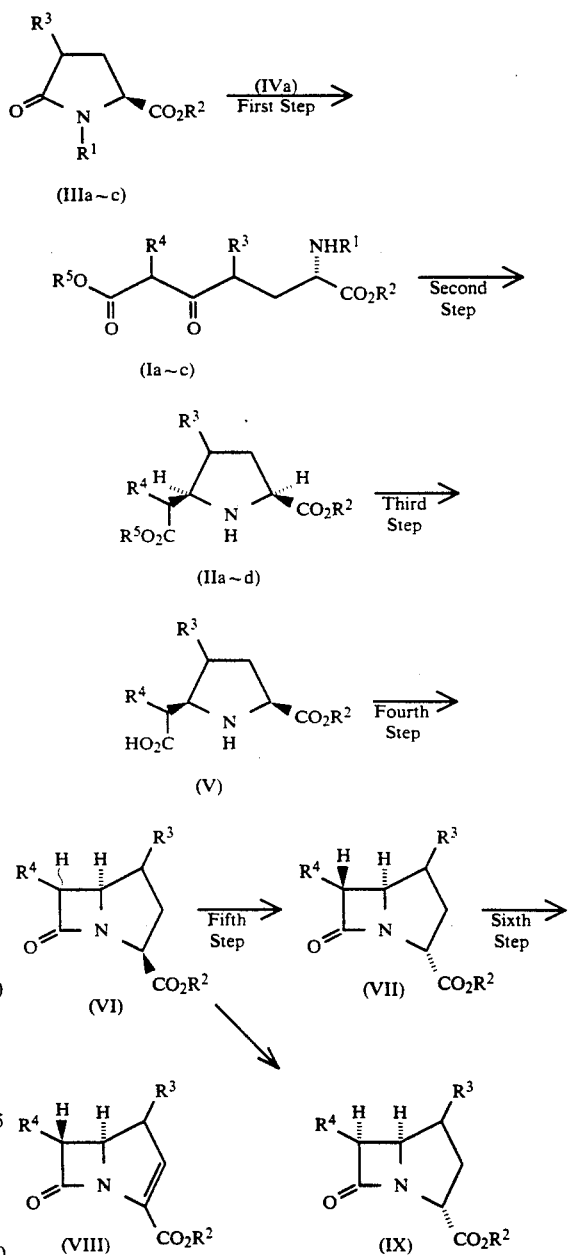

The first step is for the production of the novel amino acid derivative (I), comprising adding a carboxylic acid ester lithium enolate represented by the general formula (IVa) to the pyrrolidone carboxylic acid ester (III), wherein the amino and the carboxyl groups are both protected, and opening the pyrrolidone ring. The lithium enolate (IVa) can be formed from the carboxylic acid ester (IV), by reacting the ester (IV) with lithium di-isopropylamide.

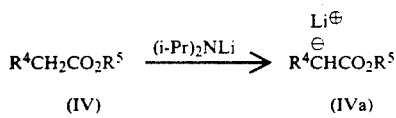

The novel reaction involving the addition of lithium enolate to the N-protected pyrrolidone carboxylic acid derivative proceeds in a good yield to give the amino acid derivative (I).

The second step produces the pyrrolidine derivative (II) stereoselectively by removing the N-protecting group from the amino acid derivative (I) and then cyclizing it under reducing conditions. The steps of removing the N-protecting group and cyclizing the product can be carried out simultaneously or separately (see the reference example below). The pyrrolidine derivative (II) can be produced in one step by employing a N-protecting group capable of being removed reductively. For the N-protecting group, a protecting group which is generally employed in the synthesis of peptides, such as benzyloxycarbonyl or p-nitrobenzyloxycarbonyl, is effective. Reduction using a palladium-carbon catalyst under a pressure of hydrogen gas between 4 and 100 kg/cm$^2$ can be used to effect simultaneously removal of the N-protecting group and cyclization.

The third step produces the carboxylic acid derivative (V) by cleaving selectively the substituent R$^5$ in the pyrrolidine derivative (II). For example, when R$^5$ is t-butyl and R$^2$ is methyl, the reaction proceeds almost quantitatively by treatment with trifluoroacetic acid (CF$_3$CO$_2$H). When R$^5$ is methyl and R$^2$ is t-butyl, the reaction proceeds almost quantitatively by hydrolysis with alkali such as equimolar NaOH. When R$^2$ is hydrogen and R$^5$ is t-butyl, a carboxylic acid (V, R$^2$=CH$_3$) can be obtained by first protecting the amino group with t-butyloxycarbonyl (BOC) (IIc), converting the group R$^2$ to a methylester (IId), and then treating it with trifluoroacetic acid.

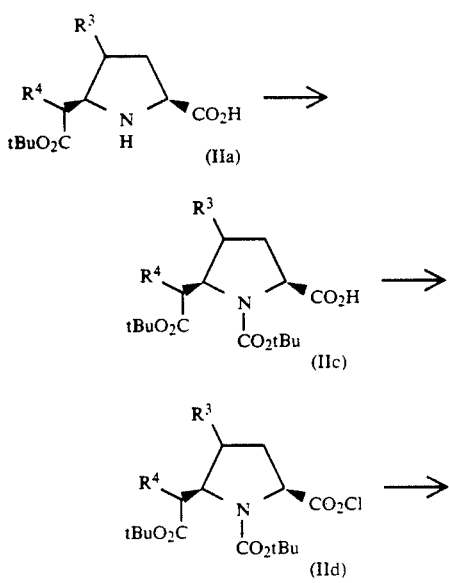

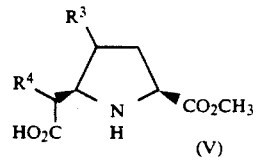

The fourth step produces compound (VI) by β-lactam cyclization through a dehydrative coupling reaction. The reaction can proceed by, for example, treatment with triphenylphosphine and 2,2'-dipyridyldisulfide in acetonitrile, or treatment with dicyclohexylcarbodiimide (DCC) in acetonitrile.

The fifth step involves regulating the stereo-configuration in the six-position in the carbapenam compound (VI) to be (R)-form or (S)-form. The compound (VI) is a (3S, 5R, 6RS)-form, which is racemic at the six-position. In order to prepare the carbapenem compound for drug effectiveness, it is desirable to produce the (R)-form or (S)-form at the six-position. The present inventors have found that (3R, 5R, 6R)-form (VII) is obtained preferentially by treating the compound (VI) with lithium di-isopropylamide (LDA) at about −78° C. and then quenching with acetic acid/methanol at about 0° C.

A sixth step produces a carbapenem by a dehydrogenation of the compound (VII) to give a double bond at the 2,3 position.

The reaction can proceed by treating the compound (VII) with a proton-removing agent such as lithium hexamethyldisilazide, reacting it with PhSeBr or PhSCl to introduce a 3-phenylthio group, treating the product with an oxidizing agent such as H$_2$O$_2$, metachloroperbenzoic acid or meta NaIO$_4$ and removing the selenoxide or sulfoxide group thus produced.

The thus obtained product (VIII) can be purified by, for example, column chromatography.

Product (VIII) in which, for example, R$^2$ is methyl, R$^3$ is hydrogen and R$^4$ is ethyl, as thus synthesized is identical with that produced by the known method (K. Prasad et al, Heterocycles, 19, 2099 (1982)), as judged by the nuclear magnetic resonance (NMR) spectrum and infra-red (IR) spectrum.

Other features of the invention will become apparent in the course of the following descriptions of exemplary embodiments which are given for illustration of the invention and not intended to be limiting.

EXAMPLES

Example 1

Synthesis of 2(S)-benzyloxycarbonylamino-5-keto-6-t-butyloxycarbonyloctanoic acid benzylester (Ia)

To an anhydrous tetrahydrofuran (THF) solution (12 ml) of LDA, which was produced from diisopropylamine (0.17 ml, 1.20 mmol) and a 15% solution of n-butyl lithium in hexane (0.76 ml, 1.20 mmol), an anhydrous THF solution (1 ml) of tert-butyl butyrate (144 mg, 1.00 mmol) was added dropwise at −78° C. under an argon atmosphere.

It was stirred for 30 minutes, and N-benzyloxycarbonyl pyrrolidone carboxylic acid benzylester (IIIa; 497 mg, 1.00 mmol) in anhydrous THF solution (4 ml) was added dropwise and further stirred for 1 hr.

After the completion of the reaction, a solution (4 ml) of a mixture of acetic acid and methanol (1:1 v/v) was added. The solution was extracted with ether and the ether layer washed with water and dried over anhydrous magnesium sulfate. The solvent was distilled off, and the thus obtained residue was subjected to silica gel chromatography.

A fraction eluted with hexane-ethyl acetate (8:2 v/v) gave the desired product (Ia; 402 mg, 81%) as a colorless oil.

IR $\nu_{max}^{neat}$ cm$^{-1}$: 3300(NH), 1735(CO$_2$), 1715(CO$_2$), 1705(C=O)

NMR (CDCl$_3$):δ0.86(3H,t,J=7Hz,CH$_3$), 1.41(9H,s,CH$_3 \times$3), 1.66-2.83(6H,m,C$_3$—H$_2$,C$_4$—H2 and C$_8$—H$_2$), 3.16(1H,t,J=7Hz,C$_6$—H), 4.03-4.73(1H,m,C$_2$—H), 5.03(2H,s,CH$_2$,Ar), 5.08(2H,s,CH$_2$Ar), 5.33(1H,d,J=8Hz,NH), 7.25(10H,s,ArH).

Molecular Weight MS m/z=497(M$^+$).

Example 2

Synthesis of 2(S)-benzyloxycarbonylamino-5-keto-6-t-butyloxycarbonyloctanoic acid methylester (Ib)

To an anhydrous THF solution (50 ml) of LDA, which was produced from diisopropylamine (1.8 ml, 12.9 mmol) and a hexane solution (8.0 ml, 12.8 mmol) of 15% n-butyl lithium, an anhydrous THF solution (3 ml) of tert-butyl butyrate (1.65 g, 11.5 mmol) was added dropwise at −75° C. under an argon atmosphere.

It was stirred for 30 minutes and an anydrous THF solution (6 ml) of N-benzyloxycarbonyl pyrrolidone carboxylic acid methylester (IIIb; 2.98 g, 10.8 mmol) was added dropwise. The solution was further stirred for 2.5 hours and the reaction mixture then poured into ice and saturated aqueous ammonium chloride and was extracted with ether. The thus extracted solution was washed with saturated aqueous sodium chloride and dried over anhydrous magnesium sulfate. It was concentrated under reduced pressure, and on thin layer chromatography (TLC) gave, as almost a single component the desired product (Ib; 4.09 g, 90%) as a light yellow oil.

IR (film) $\nu$max(cm$^{-1}$):3370, 1720, 1260, 1220, 1160, 1060, 750, 700.

NMR (CDCl$_3$):δ0.90(3H,t,J=7Hz), 1.43(9H,s) 1.75-2.25(4H,m), 2.45-2.75(2H,m), 3.23(1H,t,J=7Hz), 3.75(3H,s), 4.36(1H,m), 5.10(2H,s), 5.38(1H,m), 7.36(5H,s).

Example 3

Synthesis of 2(S)-benzyloxycarbonylamino-4-acetoxy-5-keto-6-t-butyloxycarbonyloctanoic acid benzylester (Ic)

To an anhydrous IHF solution (5 ml) of LDA, Which was produced from diisopropylamine (0.02 ml, 0.151 mmol) and a 15% solution of n-butyl lithium in hexane (0.10 ml, 0.151 mmol), an anhydrous THF solution (1 ml) of tert-butyl butyrate (14.6 mg, 0.126 mmol) was added dropwise at −78° C. It was stirred for 30 minutes and an anhydrous THF solution (2 ml) of N-benzyloxycarbonyl-4-acetoxy-5-pyrrolidone-(2S)-carboxylic acid benzylester (51.8 mg 0.126 mmol) was added dropwise and further stirred for 1 hour. After completion of the reaction, a solution (0.5 ml) of acetic acid and methanol (1:1, v/v) was added and extracted with ether. The extracted ether layer was washed with water and dried over anhydrous magnesium sulfate. The solvent was distilled off and the thus obtained residue was subjected to silica gel chromatography. A fraction eluted with n-hexane and ethyl acetate (4:1, v/v) gave the desired product (Ic; 33.6 mg, 48%) as a light yellow oil.

IR (CHCl$_3$) $\nu$max(cm$^{-1}$):3620-3200(NH), 1740, 1720, 1715

NMR (CDCl$_3$):δ0.84(3H,t,J=7Hz), 1.45(9H,s), 1.90-2.39(4H,m), 2.05(3H,s), 3.48-3.75(1H,m), 4.40-4.75(2H,m), 5.05(2H,s), 5.10(2H,s), 5.20-5.60(1H,m), 7.25(10H,s).

Example 4

Synthesis of 5(R)-(1'(RS)-t-butyloxycarbonyl)-propylpyrrolidine-2(S)-carboxylic acid (IIa)

To the methanol solution (90 ml) of the octanoic acid derivative (Ia; 1.80 g, 3.64 mmol), as obtained in Example 1, 5% palladium-carbon (Pd-C; 180 mg) was added and catalytic reduction (4 kg/cm$^2$, H$_2$) was carried out for 16 hours. After a completion of the reaction, the catalyst used was removed by filtering with cellite.

The solvent was distilled off and the thus obtained residue subjected to silica gel chromatography. A fraction eluted with a mixture of acetonitrile and methanol (7:3, v/v) gave the desired product (IIa; 728 mg, 78%) as colourless needles.

Melting point 156°-158° (dec.).

IR $\nu_{max}^{KBr}$ cm$^{-1}$: 3400(NH$_3$), 1720(CO$_2$), 1620(CO$_2^-$)

NMR (CD$_3$OD):δ1.00(3H,t,J=7Hz,CH$_3$), 1.46(9H,s,CH$_3 \times$3), 1.46-3.00(7H,m,C$_3$—H$_2$,C$_4$—H$_2$,-C$_6$—H,C$_8$-H$_2$) 3.40-3,80(1H,m,C$_5$—H), 3.80-4.18(1H,m,C$_2$—H).

MS m/z=257 (M$^+$).

Example 5

Synthesis of 5(R)-(1'(RS)-t-butyloxycarbonyl)-propylpyrrolidine-2(S)-carboxylic acid methylester (IIb) Method A Octanoic acid derivative (Ib) as obtained in Example 2 (1.00 g, 2.37 mmol), methanol (25 ml), acetic acid (0.43 g, 7.2 mmol), and 10% palladium-carbon (100 mg) were placed in a stainless steel autoclave having an internal volume of 100 ml. Hydrogen gas (80 kg/cm$^2$) was passed into it and the reaction was stirred for 14 hours at room temperature.

The palladium-carbon was removed by filtration, and the filtrate was concentrated, and an ethyl acetate solution was prepared. It was washed with 5% aqueous sodium bicarbonate (NaHCO$_3$) solution, then with saturated aqueous sodium chloride solution, and dried over anhydrous sodium sulfate. It was concentrated under reduced pressure to give the desired product (IIb; R$^2$=methyl, R$^3$=H, R$^4$=ethyl, R$^5$=t-butyl) as a light yellow liquid (477 mg, 74%).

IR (neat) $\nu$max (cm$^{-1}$):1732.

NMR (CDCl$_3$):δ0.89.–0.96(3H,tt,7.8Hz), 1.46(s), 1.48(s), 1.30-1.75(m)(total 11H), 1.80-2.00(3H,m), 2.00-2.15(1H,m), 2.20-2.30(1H,m), 3.12-3.28(1H,m), 3.72(s) 3.73(s), 3.7-3.8(m)(total 4H).

Example 6

Synthesis of 1-t-butyloxycarbonyl-5(R)-(1'(RS)-t-butyloxycarbonyl)-propylpyrrolidine-2(S)-carboxylic acid methylester (IId)

To the solution (15 ml) of mixture of dioxane and water (2:1,v/v) of the product (IIa, 748 mg, 2.91 mmol) as obtained in Example 4, triethyl amine (0.61 ml, 4.37 mmol) was added and then di-tert-butylcarbonate (0.74 ml, 3.20 mmol) was added dropwise at 0° C. The reaction mixture was stirred for 30 minutes, then the solution was heated to a room temperature and it was further stirred for 3 hours. After completion of the reaction, water was added, and the solution was washed with ether. The water layer was acidified with citric acid and extracted with ethyl acetate. The ethyl acetate layer was washed with water and dried with anhydrous magnesium sulfate. The solvent was distilled off and the carboxylic acid (IIc; 1.05 g) was obtained.

To a methanol solution (10 ml) of the carboxylic acid (IIc; 1.05 g), an ether solution of diazomethane was added dropwise at 0° C. until it showed a yellow colour continuously, and then it was allowed to stand for 30 minutes. After the completion of the reaction the solvent was distilled off. The thus obtained residue was subjected to silica gel chromatography. A fraction eluted with a mixture of n-hexane and ethyl acetate (9:1, v/v) gave the desired product (IId; 942 mg, 87%) as a colorless oil.

$Ir\nu_{max}^{neat}$ cm$^{-1}$: 1730 ($CO_2$), 1710($CO_2$), 1690(N—$CO_2$)

NMR (CDCl$_3$):δ0.93(3H,t,J=8Hz), 1.53(18H,s,CH$_3$×6), 1.63–2.19(5H,m,C$_3$—H$_2$,C$_4$—H$_2$ and C$_8$—H), 2.25–2.43(1H,m,C$_8$—H), 2.90–3.00, 3.03–3.13(1H, each m,C$_6$—H), 3.75(3H,s,COOCH$_3$), 4.03–4.41(2H,m,C$_2$—H and C$_3$—H).

MS m/z=371(M$^+$).

Example 7

Synthesis of 6-ethyl-carbapenam-3-carboxylic acid methylester (3S, 5R, 6RS) (VI) Method (A)

To an anisole solution (0.3 ml) of the ester (IId; 52 mg, 0.14 mmol) as obtained in Example 6, trifluoroacetic acid (TFA) (1.0 ml) was added dropwise at 0° C. It was stirred for 2.5 hours. After completion of the reaction, it was diluted with water and washed with ether. From the water layer the solvent was distilled off, and the carboxylic acid derivative (V) TFA salt (60 mg) was obtained.

To an anhydrous acetonitrile-benzene solution (1:1 v/v) (7 ml) of triphenylphosphine (53 mg, 0.20 mmol) and 2,2'-dipyridyl disulfide (44 mg, 0.20 mmol), triethylamine (0.02 ml, 0.14 mmol) was added. The solution was heated under reflux and an anhydrous acetonitrile-benzene solution (1:1, v/v) (5 ml) of the carboxylic acid derivative (V) TFA salt (60 mg) was added dropwise over 2 hours. It was further heated under reflux for 30 minutes and then cooled to room temperature. The solvent was distilled off. The thus obtained residue was diluted with ether and insoluble matter removed by filtration. The solvent was distilled off. The thus obtained residue was subjected to silica gel column chromatography and a fraction eluted with a mixture of n-hexane and ethyl acetate (7:3, v/v) gave a carbapenam (VI; 16 mg, 57%). According to a $^1$H NMR analysis, it was a mixture of (6R) derivative and (6S) derivative in a ratio of ~1:1.

$IR\nu_{max}^{CHCl3}$ cm$^{-1}$: 1758(N—C=O), 1740($CO_2$)

NMR (CDCl$_3$):δ0.99, 1.02(3H, each t,J=8Hz, CH$_3$), 1.63–2.40(6H,m,C$_3$—H$_2$,C$_4$—H2 and C$_8$—H$_2$), 2.83–2.96, 3.08–3.16(1H, each m, C$_6$—H), 3.53–3.60, 3.70–3.80(1H, each m,C$_5$—H), 3.75(3H,s,CO$_2$CH$_3$), 3.88(1H,dd,J=8 and 1.5Hz, C$_2$—H).

MS m/z=197(M$^+$) (Found: 197.1044; Calculation for C$_{10}$H$_{15}$NO$_3$:197.1051).

Example 8

Synthesis of 6-ethyl-carbapenam-3-carboxylic acid methylester (3S, 5R, 6RS) (VI) Method (B)

4N hydrogen chloride dioxane solution was added to the ester (IIb) (477 mg, 1.76 mmol) as obtained in Example 5, and the thus obtained mixture was stirred for 3 hours at a temperature of between 20° C. and 25° C. The reaction solution was concentrated under reduced pressure to give the carboxylic acid hydrochloride derivative (R$^2$=methyl, R$^3$=H, R$^4$=ethyl) as a light brown paste-like material. It was not further purified, but was dissolved in dichloromethane, and triethylamine (0.26 ml, 1.9 mmol) was added. Then a dichloromethane solution of N,N'-dicyclohexylcarbodiimide (DCC) (435 mg, 2.1 mmol) was added under cooling with ice, and the mixture was stirred for 15 hours at a temperature of between 20° C. and 25° C. The reaction mixture was concentrated and ether was added. Insoluble matter was removed by filtration, and the thus obtained filtrate was concentrated under reduced pressure. The thus obtained residue was purified by silica gel chromatography to give the desired product (VI) as a light yellow liquid (250 mg, yield 72% based on the product (IIb)).

The six-position of this compound (VI) is a mixture of (R) and (S) derivatives in the ratio of 1:1. The spectral data of this compound are all identical with those of the product obtained in Example 7.

Example 9

Synthesis of 6-ethyl-carbapenam-3-carboxylic acid methylester (3R, 5R, 6R) (VII)

To an anhydrous THF solution (3 ml) of LDA, as produced from diisopropylamine (0.04 ml, 0.20 mmol) and a 15% n-butyllithium hexane solution (0.14 ml, 0.20 mmol), an anhydrous THF solution (2 ml) of the carbapenam (VI) (17 mg, 0.09 mmol) as obtained in Example 7 or 8 was added dropwise at −78° C. under a current of argon. The mixture was stirred for 30 minutes and warmed to 0° C., and a mixture of acetic acid and methanol (1:1, v/v) (0.5 ml) was added thereto. It was extracted with ether. The ether layer was washed with water and dried on anhydrous magnesium sulfate. The solvent was distilled off and the thus obtained residue was subjected to high performance liquid chromtography (HPLC) and the fraction eluted with a mixture of n-hexane and ethyl acetate (9:1, v/v) gave as a low polar fraction a mixture (2 mg) of a carbapenam in the 5,6-cis form (IX) and a small amount of a by-product, and gave a carbapenam (VII) in the 5,6-trans form (VII) (9 mg, 50%) as a high polar fraction.

Specific Rotation $[\alpha]_D^{20}$= +179.5° (C=0.22, CHCl$_3$).

IR$\nu_{max}^{CHCl_3}$ cm$^{-1}$: 1760(N—C=O), 1745(CO$_2$)

NMR(CDCl$_3$):δ1.00(3H,t,J=8Hz, CH$_3$), 1.65-2.45(4H,m,C$_3$—H$_2$ and C$_4$—H$_2$), 2.67-2.75(1H,m,C$_6$—H), 3.50-3.58(1H,m,C$_5$—H), 4.34(1H,t,J=8Hz, C$_2$—H), MS m/z=197(M+) (Calcd 197.1051 for C$_{10}$H$_{15}$NO$_3$; Found 197.1057)

Example 10

Synthesis of 6-ethyl-carbapenam-3-carboxylic acid methylester (3R, 5R, 6S) (IX)

To an anhydrous THF solution (3 ml) of LDA, as produced from diisopropylamine (0.03 ml, 0.19 mmol) and a 15% n-butyllithium hexane solution (0.12 ml, 0.19 mmol), anhydrous THF solution (2 ml) of the carbapenam (VI) (16 mg, 0.08 mmol) was added dropwise at −78° C. under a carbapenam (VI) (16 mg, 0.08 mmol) was added dropwise at −78° C. under a current of argon. The mixture was stirred for 30 minutes and a mixture of acetic acid and methanol (1:1, v/v) (0.5 ml) was added. It was warmed to room temperature and extracted with ether. The ether layer was washed with water and dried with anhydrous magnesium sulfate. The solvent was distilled off and the thus obtained residue was subjected to HPLC purification. A fraction eluting with a mixture of n-hexane and ethyl acetate (9:1, v/v) gave a mixture (12 mg) of a carbapenam in the 5,6-cis form (IX) with a small quantity of by-product.

IR$\nu_{max}^{CHCl_3}$ cm$^{-1}$: 1760(N—CO=O), 1740(CO$_2$)

NMR (CDCl$_3$):δ0.93(3H,t,J=8Hz, CH$_3$), 1.34-2.03(4H,m,C$_3$—H$_2$ and C$_4$—H$_2$), 2.12-2.21(1H,m,C$_8$—H), 2.31-2.41(1H,m,C$_8$—H), 3.25-3.30(1H,m,C$_6$—H), 3.65(3H,s,CO$_2$CH$_3$), 4.46(1H,t,J=8Hz,C$_2$—H)

MS m/z=197(M+) (Calcd 197.1051 for C$_{10}$H$_{15}$NO$_3$; Found 197.1070)

Example 11

Synthesis of 6-ethyl-carbapenem-3-carboxylic acid methylester (5R, 6R) (VIII)

To an anhydrous THF solution (15 ml) of lithium hexamethyl disilazide, as produced from hexamethyl disilazane (194 mg, 1.20 mmol) and a 15% n-butyllithium hexane solution (0.68 ml, 1.10 mmol), an anhydrous THF solution (5 ml) of the carbapenam (86 mg, 0.40 mmol) obtained in Example 9 was added dropwise at −78° C. under a current of argon. The mixture was stirred for 30 minutes and a THF solution (5 ml) of phenylselenyl chloride (230 mg, 1.20 mmol) was added. It was further stirred for 30 minutes, then elevated to room temperature and stirred for 1 hour. The reaction mixture was added to a mixture of methylene chloride and saturated aqueous sodium choride for extraction. The methylene chloride layer was washed with water and dried over anhydrous sodium sulfate. The solvent was distilled off, and the thus obtained crude product was dissolved in methylene chloride (30 ml) and cooled to −30° C. m-Chloroperbenzoic acid (52.5 mg, 0.305 mmol) was added and the mixture was stirred for 15 minutes, and then triethylamine (65 μl, 0.46 mmol) was added. The mixture was warmed to room temperature and washed with saturated aqueous sodium bicarbonate solution and dried over anhydrous sodium sulfate. The mixture was concentrated under reduced pressure, and the thus obtained residue was subjected to HPLC purification. A fraction eluting with a mixture of n-hexane and ethyl acetate (2:1, v/v) gave the carbapenem (VIII) 32 mg, 10.17 mmol, 38.6%).

IR (cm$^{-1}$):1770, 1718.
NMR (CDCl$_3$):δ1.05(3H,t,J=7.4Hz), 1.78-1.97(2H,m). 2.76(1H,ddd,J=19.0Hz,8.3Hz,2.8Hz), 2.93(1H,ddd,J=19.0Hz,9.8Hz,2.9Hz), 3.18(1H,ddd,J=7.1Hz,5.6Hz,3.0Hz), 3.84(3H,s), 4.00(1H,ddd,J=9.8Hz,8.3Hz,3.0Hz), 6.46(1H,J=2.9Hz,2.8Hz).
MS m/z=195(M+).

Reference Example

Synthesis of 5(R)=(1'(RS)-t-butyloxycarbonyl)propylpyrrolidine-2(S)-carboxylic acid methylester (IIb) Method (B)

To the methanol solution (50 ml) of the amino acid derivative (Ib) (1.0 g, 2.38 mmol) obtained in Example 2, 5% palladium-carbon (100 mg) was added and a catalytic reduction reaction using a Pear apparatus was carried out for 16 hours (4 kg/cm$^2$, H$_2$). The catalyst was removed by filtration and the solution concentrated under reduced pressure. On TLC, an enamine form (X) (0.62 g, 97%), which was the single product, was obtained as a colorless oil.

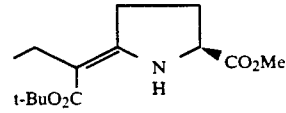
(X)

IR (film) νmax(cm$^{-1}$):3360, 1740, 1660, 1600.
NMR (CDCl$_3$):δ0.95(3H,t,J=7Hz), 1.45(9H,s), 1.80-2.45(6H,m), 2.55-2.75(2H,m), 3.46(1H,s), 3.72(3H,s), 4.25-4.35(1H,m).

This product (X) (189 mg, 0.70 mmol) was subjected to a catalytic reduction reaction under a high pressure (80 kg/cm$^2$) in the same manner as in Example 5. It was reacted for 24 hours at room temperature and the catalyst removed. The thus obtained filtrate was concentrated and an ethyl acetate solution prepared. The solution was washed with 5% NaHCO$_3$ aqueous solution and then saturated NACl aqueous solution, dried over anhydrous sodium sulfate, and concentrated under reduced pressure to give the desired product (IIb) (133 mg, 70%).

The spectrum of the product (IIb) obtained above was entirely identical with the compound synthesized in Example 5.

Example 12

Synthesis of 2(S)-benzyloxycarbonylamino 5-keto-6-t-butyloxycarbonylheptanoic acid benzylester (Id)

To an anhydrous THF solution (12 ml) of LDA, which was produced from diisopropylamine (0.17 ml, 1.20 mmol) and a 15% n-butyl lithium hexane solution (0.76 ml, 1.20 mmol), an anhydrous THF solution (1 ml) of tert-butyl propionate (130 mg, 1.00 mmol) was added dropwise at −75° C. under an argon atmosphere.

It was stirred for 30 minutes and the anhydrous THF solution (4 ml) of N-benzyloxycarbonyl pyrrolidone carboxylic acid benzylester (IIIa, 353 mg, 1.00 mmol) was added dropwise thereto. It was further stirred for 30 minutes. After the reaction was completed, a mixture (0.5 ml) of acetic acid and methanol (1:1, v/v) was added thereto and was extracted with ether. The thus obtained ether layer was washed with water and dried over anhydrous magnesium sulfate. The solvent was distilled off from the mixture and the thus obtained residue subjected to silica gel chromatography. A fraction eluted with n-hexane-ethyl acetate (8:2, v/v) gave the desired product (Id, 448 mg, 93%) as a colorless oil.

IR$\nu_{max}^{neat}$ cm$^{-1}$: 3325, 1750, 1735, 1710, 1690

NMR(CDCl$_3$):δ1.26(3H,d,J=7.0Hz), 1.46(9H,S), 1.91-2.81(4H,m), 3.33(1H,q,J=7.0Hz), 4.36(1H,ddd,J=2.0, 8.0 and 16.0Hz), 5.08(2H,S), 5.15(2H,S), 5.45(1H,d,J=8.0 Hz), 7.26(10H,S).
MS m/Z=426(M+ −57).

Example 13

Synthesis of 2(S)-benzyloxycarbonylamino-5-keto-6-t-butyloxycarbonyl-7-methyloctanoic acid benzylester (Ie)

To an anhydrous THF solution (12 ml) of LDA, which was produced from diisopropylamine amine (0.17 ml, 1.20 mmol) and a 15% n-butyl lithium hexane solution (0.76 ml, 1.20 mmol), an anhydrous THF solution (1 ml) of tert-butyl isovalerate (158 mg, 1.00 mmol) was added dropwise at −78° C. under an argon atmosphere.

It was stirred for 30 minutes and an anhydrous THF solution (6 ml) of N-benzyloxycarbonyl pyrrolidone carboxylic acid benzylester (IIIa; 353 mg, 1.00 mmol) was added dropwise. It was further stirred for 30 minutes. After the reaction was completed, a mixture (0.5 ml) of acetic acid and methanol (1:1, v/v) was added and extracted with ether. The thus extracted ether solution was washed with water and dried over anhydrous magnesium sulfate. The solvent was distilled off from the mixture and the thus obtained residue was subjected to silica gel chromatography. A fraction eluted with n-hexane-ethyl acetate (8:2, v/v) gave a colorless oil. It was recrystallized with dichloromethane/n-hexane to obtain the desired product (Ie; 422 mg, 83%) as colorless needle-like crystals.
Melting point 69-71° C.

Ir$\nu_{max}^{neat}$ cm$^{-1}$: 3325, 1750, 1730, 1715, 1695

NMR(CDCl$_3$):δ0.83(3H,d,J=6.0Hz),
0.98(3H,d,J=6.0Hz), 1.40(9H,s),
1.66-2.78(5H,m),3.03(1H,d, J=8.0Hz),
3.95-4.56(1H,m) 5.00(2H,s), 5.10(2H,s),
5.43(1H,d,J=8.0HZ), 7.22 (10H,s).
MS m/Z=454 (M+ −57).

Example 14

Synthesis of 2(S)-benzyloxycarbonylamino-5-keto-6-t-butyloxycarbonyl-7-phenylheptanoic acid benzylester (If)

To an anhydrous THF solution (12 ml) of LDA, which was produced from diisopropylamine (0.17 ml, 1.20 mmol) and a 15% n-butyl lithium hexane solution (0.76 ml, 1.20 mmol) an anhydrous THF solution (1 ml) of tert-butyl phenylpropionate (206 mg, 1.00 mmol) was added dropwise at −78° C. under an argon atmosphere.

It was stirred for 30 minutes and an anhydrous THF solution (4 ml) of N-benzyloxycarbonyl pyrrolidone carboxylic acid benzylester (IIIA, 353 mg, 1.00 mmol) was added dropwise. It was further stirred for 30 minutes. After the reaction was finished, a mixture (0.5 ml) of acetic acid and methanol (1:1, v/v) was added and extracted with ether. The thus obtained ether layer was washed with water and dried over anhydrous magnesium sulfate. The solvent was distilled off from the mixture and the thus obtained residue was subjected to silica gel chromatography. A fraction eluted with n-hexane-ethyl acetate (8:2, v/v) gave the desired product (If, 452 mg, 81%) as a colorless oil.

IR$\nu_{max}^{neat}$ cm$^{-1}$: 3400, 1750, 1735, 1720, 1700

NMR(CDCl$_3$):δ1.37(9H,s), 1.73-2.93(4H,m) 3.08(2H,d,J=7.0Hz), 3.65(1H,dd,J=6.0 and 10.0Hz), 4.31 (1H,ddd,J=2.0, 8.0 and 16.0Hz), 5.05 (2H,s), 5.10(2H,s), 5.30 (1H,d,J=7.0), 6.90-7.43(10Hz,m).
MS m/Z=502(M+ −57).

By means of the present invention carbapenam and carbapenem compounds can be produced in short steps and in high yield, using a relatively cheap glutamic acid derivative as a starting material. Moreover, several novel and highly active carbapenam and carbapenem compounds can be produced.

Obviously, numerous modifications and variations of the present invention are possible in light of the above teachings. It is therefore to be understood that within the scope of the appended claims, the invention may be practiced otherwise and as specifically described herein.

What is claimed as new and desired to be secured by Letters Patent of the United States is:

1. A process comprising
(i) selectively cleaving the substituent R$^5$ from a compound of the formula (II)

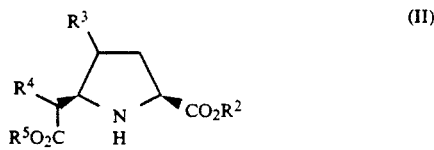

wherein R$^2$ is hydrogen or a carboxylic-protecting group, R$^5$ is a carboxylic-protecting group, R$^3$ is hydrogen, alkyl, hydroxyl, methoxy or acetoxy, R$^4$ is methyl, ethyl, i-propyl, benzyl or a CH$_3$CR$^6$(OR$^7$)-group in which R$^6$ is hydrogen or methyl and R$^7$ is hydrogen or a hydroxyl-protecting group and having, respectively 2(S) and 5(R) configurations in the 2 and 5 positions thereof;
to give a compound of the formula (V)

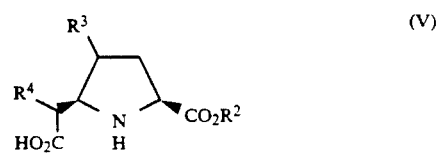

(ii) β-lactam cyclizing the compound of the formula (V) to produce a compound of the formula (VI);

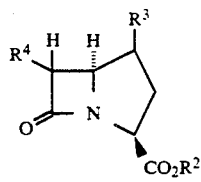

(VI)

(iii) treating the compound of the formula (VI) with lithium diisopropylamide at about −78° C. and quenching said treated compound with acetic acid/methanol at about 0° C. to give predominantly the (3R, 5R, 6R)

carbapenem compound (VII)

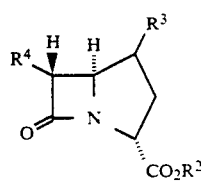

(VII)

or quenching the compound of the formula (VI) at about −78° C. to give predominantly the (3R, 5R, 6S) carbapenam compound (IX)

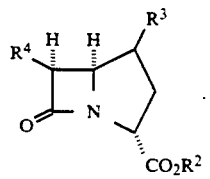

(IX)

2. The process of claim 1 wherein said carboxylic-protecting group is an alkyl, aralkyl or alkaryl group, and the hydroxyl-protecting group is a benzyl, benzyloxycarbonyl, t-butyldimethylsilyl or trichloroethyloxycarbonyl group.

3. The process of claim 1, further comprising:
    (iv) dehydrogenating the carbapenam compound (VII) to produce the (5R, 6R) carbapenem compound (VIII)

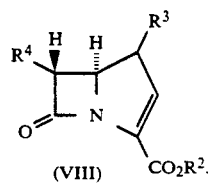

(VIII)

4. The process of claim 3 wherein said dehydrogenating step (iv) is carried out by treating the carbapenam compound (VII) with a proton-removing agent, reacting said treated compound with PhSeBr or PhSCl to introduce a 3-phenylseleno or 3-phenylthio group, treating the product of said reacting step with an oxidizing agent and removing the selenoxide or sulfoxide thus produced.

5. The process of claim 4 wherein the proton-removing agent is lithium hexamethyldisilazide.

* * * * *